United States Patent [19]

Cuttitta et al.

[11] Patent Number: 5,460,801
[45] Date of Patent: Oct. 24, 1995

[54] INHIBITION OF SMALL CELL LUNG CANCER CELL GROWTH IN VIVO USING MONOCLONAL ANTIBODY

[75] Inventors: Frank F. Cuttitta, Adamstown; John D. Minna, Bethesda, both of Md.

[73] Assignee: The United States of America as represented by the Department of Health and Human Services, Washington, D.C.

[21] Appl. No.: 47,006

[22] Filed: Apr. 15, 1993

Related U.S. Application Data

[60] Continuation of Ser. No. 695,004, May 3, 1991, abandoned, which is a division of Ser. No. 281,951, Dec. 5, 1988, Pat. No. 5,109,115, which is a continuation of Ser. No. 717,692, Mar. 29, 1985, abandoned.

[51] Int. Cl.$^6$ .................................................. A61K 39/395
[52] U.S. Cl. ..................................... 424/138.1; 424/139.1; 424/152.1; 424/155.1; 424/158.1
[58] Field of Search ........................... 424/85.8, 130.1, 424/138.1, 139.1, 141.1, 152.1, 155.1, 158.1; 530/387.1, 387.7, 388.1, 388.8

OTHER PUBLICATIONS

Waldman Science 252: 1657–1662 (1991).
Cuttitta et al. Nature 316: 823–826 (1985).
Moody et al. Science 214: 1246–1248 (1981).
Cuttitta et al. Clinical Research 31: 405A (1983).
Moody Peptides 4: 683–686 (1983).
Cuttitta et al. Monoclonal Antibodies in Cancer pp. 161–180 (1984).
Osband et al. Immunol. Today 11: 193–195 (1990).
Steiner et al. Biotechnology 11: 644 (1993).
Harris et al. Tibtech 11: 42–44 (1993).
Goding in Monoclonal Antibodies: Principles and Practice Academic Press, 1983 pp. 56–97.
Cuttitta et al., Science 158: 1570–1574 (1967).

*Primary Examiner*—David L. Lacey
*Assistant Examiner*—Phillip Gambel
*Attorney, Agent, or Firm*—Foley & Lardner

[57] ABSTRACT

The present invention discloses anti-bombesin monoclonal antibody and a method of detecting autocrine growth factor. A method and kit for screening and controlling growth of human SCLC has also been disclosed.

3 Claims, 8 Drawing Sheets

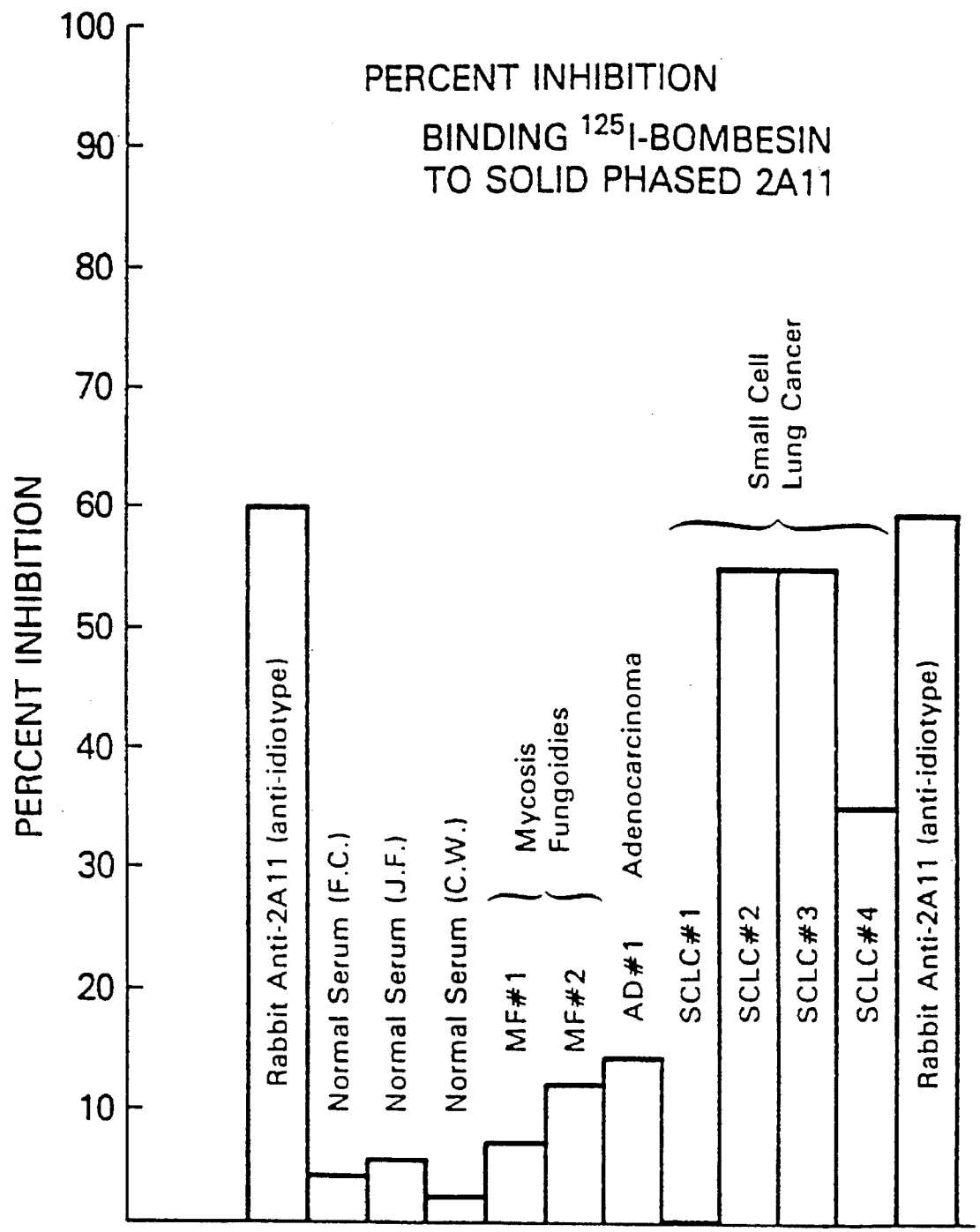

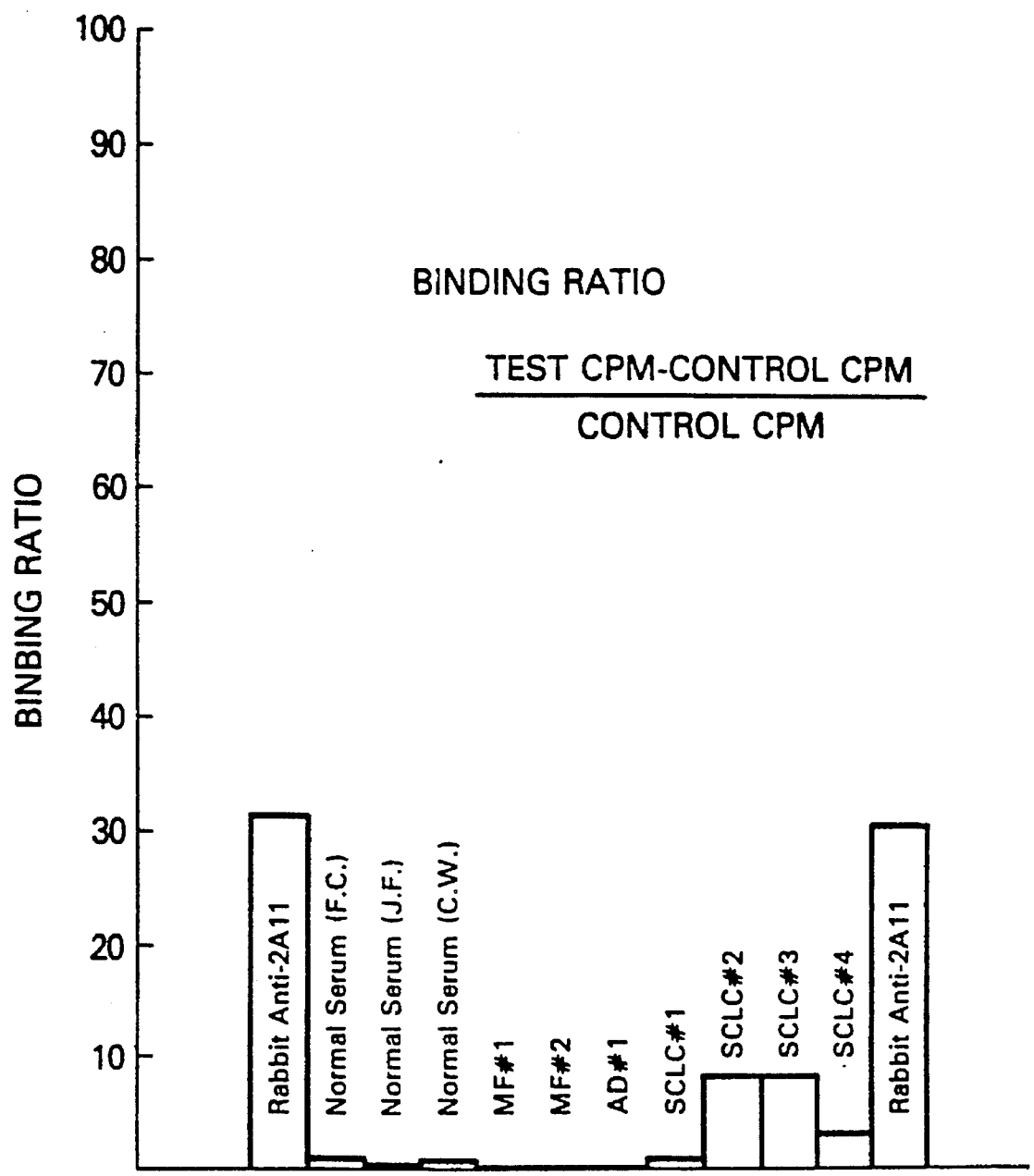

INHIBITION OF SMALL CELL LUNG CANCER CELL GROWTH IN VIVO USING MONOCLONAL ANTIBODY

This is a continuation of application No. 07/695,004, filed on May 3, 1991, which was abandoned upon the filing hereof which is a Divisional of Ser. No. 07/281,951 filed Dec. 5, 1988, now issued as U.S. Pat. No. 5,109,115; which is a continuation of Ser. No. 06/717,692 filed Mar. 29, 1985, now abandoned.

BACKGROUND OF INVENTION

1. Technical Field

The present invention relates to human small cell lung cancer (SCLC) autocrine growth factors and monoclonal antibody blocking the same. More particularly, the present invention relates to anti-bombesin monoclonal antibody blocking bombesin-receptor interaction at appropriate binding sites and inhibiting tumor growth dependent on bombesin autocrine function.

2. Prior Art

Autocrine hypothesis for tumor growth proposes that a cancer cell produces a growth factor(s) which in turn stimulates the growth of the cancer cell resulting in a malignant phenotype (Sporn, et al. *New Eng. J. Med.* 303, (1980). If this hypothesis is demonstrated to be true, then it would be apparent that by interfering with this autocrine pathway, one could potentially block tumor cell growth dependent on said autocrine growth factor.

By definition autocrine growth factors comprise hormone-like substances produced and secreted by normal or malignant cells which in turn "feed back" on these cells via specific membrane receptors to induce proliferation of the cells. Although many growth factors (epidermal growth factor [EGF], transforming growth factors [TGF], platelet-derived growth factor [PDGF], T-cell growth factor [ITCGF], nerve growth factor [NGF] and the like have been shown to exert their influence on the propagation of normal and malignant cells in vitro, none so far has been conclusively proven to fulfill all the autocrine properties including control of tumor proliferation in vitro.

Lung cancers have been the prime example of tumors which produce peptide hormones. Within this group, human small cell lung cancer (SCLC) has been shown to produce regulatory peptides such as calcitonin, adrenocorticotrophic hormone (ACTH), arginine vasopressin (AVP), neurotensin and bombesin. Bombesin is the most frequently produced peptide hormone associated with SCLC; therefore, it has been considered a putative autocrine growth factor involved with SCLC.

Bombesin is a tetradecapeptide originally isolated and characterized by Anastasi, et al. *Experientia* 27, 166–167 (1971) from frog skin. Immunoreactive bombesin-like peptides (BLP) have also been identified in fish, birds, and mammals indicating evolutionary conservation. Biochemical and immunohistochemical analyses have localized BLP to certain brain nuclei, to amine precursor uptake and decarboxylation (APUD) cells of the fetal lung, and to gastrointestinal tract of rat and man as well as the proventriculus of turkeys. The mammalian equivalent of bombesin is thought to be gastrin-releasing peptide (GRP), a 27 amino acid long peptide initially isolated from porcine gut as described by McDonald, et al, *Gut,* 19: 767. (1978). Bombesin and GRP have nearly identical amino acid sequences at their carboxy-terminal (C-terminal) decapeptide.

The carboxy-terminal region of the bombesin molecule is believed to be responsible for receptor recognition and biological activity. Recent reports have demonstrated that both bombesin and GRP can induce similar biological responses (Brown, et al. *Life Sci.* 27, 125–128 (1980; Rokaeus, et al. *Acta Physiol. Scand.* 114, 605–610 (1982); Girard, et. al. *Neuropeptides* 3, 443–452 (1983); McDonald, et. al. Regul. *Peptides* 5, 125–137 (1983). Immunoreactive GRP has been identified in the gastrointestinal tract of mice, rats, guinea-pigs and cats. Amino acid sequences of three canine intestinal peptides have revealed close homology with porcine GRP and contain identical C-terminal decapeptide residues as bombesin and GRP (Reeve, et al *J. Bio. Chem.* 258, 5582–5588 (1983). In humans, GRP has been identified in neuro-endocrine cells of the stomach, fetal and adult lung and in small cell and carcinoid lung tumors. (Tsutsumi, et el. *Lab. Invest.* 48, 623–631 (1983); Yamaguchi, et el. *Cancer Res.* 43, 3932–3939 (1983); Tobe, et al. *Acta Histochem. Cytochem.* 15, 102–107 (1982); Tamai, et al. *Cancer* 52, 273–281 (1983); Yang, et el. *Cancer* 52, 819–823 (1983).

In recent reviews, bombesin (BN) and bombesin-like peptides (BLP) have been reported to initiate a wide variety of physiological responses including stimulation of SCLC. BLP produced by SCLC include some peptides similar, if not identical, to porcine GRP. These peptides can be secreted into media in response to physiologic stimuli. In addition, some SCLC have single class of high affinity receptors for BLP (Moody, et al. *Peptides* 4, 683–686 (1983). Moreover, exogenously added BLP can stimulate the clonal growth of SCLC in serum-free medium (Carney, et al. *Clin. Res.* 31, 404A (1983). Taken together, these findings suggest, but do not prove, that BLP could function as an autocrine growth factor for SCLC. The applicants conceived that one way to test such a hypothesis would be to interrupt the function of endogenously produced BLP in SCLC. The applicants reasoned that this could be accomplished by producing antibodies specific to BN or BLP.

SUMMARY OF INVENTION

It Is, therefore, an object of the present invention to produce monoclonal antibody capable of specifically binding with bombesin or bombesin-like peptides.

It is another object of the present invention to provide an anti-bombesin monoclonal antibody capable of blocking bombesin-receptor interaction at suitable binding sites.

It is a further object of the present invention to provide an anti-bombesin monoclonal antibody capable of inhibiting, controlling or disrupting bombesin-dependent autocrine growth of tumor cells, particularly of small cell lung cancer.

It is a still further object of the present invention to provide an anti-bombesin monoclonal antibody having diagnostic and therapeutic utility against small cell lung cancer in humans.

These and other objects and advantages of the present invention will become apparent as the description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 6a Tumor growth of melanoma cell line NCI-H234; FIG. 6b Tumor growth of SCLC cell line NCI-H592.

FIG. 7(A,B) shows detection and determination of anti-idiotypic antibodies present in the serum of SCLC patients.

DETAILED DESCRIPTION OF INVENTION

Figure 1:
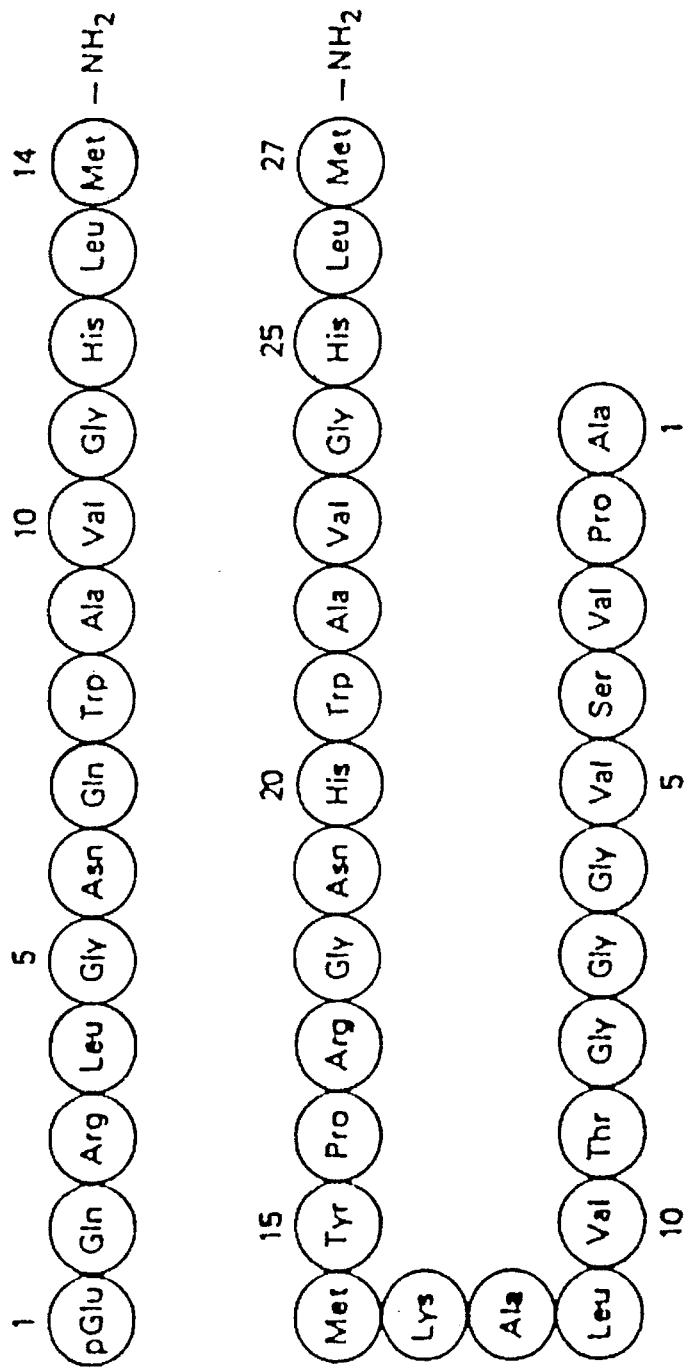
FIG. 1 shows comparison of the amino acid sequence of amphibian bombesin and porcine gastrin-releasing peptide (GRP). Regions of identical amino acid residues are indicated by shaded areas.

These and other objects and advantages of the present invention are achieved by monoclonal antibodies having specificity to bind with BN or BLP. A deposit of a hybridoma which produces the 2A11 monoclonal antibody was deposited on Jan. 31, 1985 at the American Type Culture Collection, 12301 Parklawn Drive, Rockville, Md. 20852, under accession number HB8711.

Various methods and materials employed in conducting the tests are now described. All publications cited hereunder are incorporated herein by reference.

A. HYBRIDOMA SCREENING ASSAY FOR ANTI-BOMBESIN ACTIVITY

Hybridoma supernatants were evaluated for their ability to bind solid phase BN, Substance P and bovine serum albumin (BSA). Only those hybrids having exclusive BN binding were selected.

Preparation of solid-phase Peptide Target Plates. 50 µl of a 10 µg/ml Peptide solution (BN/SubP) in phosphate buffered saline (PBS) is added to each well of a 96 well polyvinyl chloride microtiter plate (Dynatech) and adsorbed for 1 hr. at room temp. (22°–27° C.), washed 3× in PBS, then coated with 1% BSA-PBS solution to block non-specific binding sites. Plates are washed 3× in PBS and 25 µl of Test hybridoma supernatant added to respective target plates (i.e. BN, SubP or BSA), incubated 1 hr., washed 3× in PBS and then protein A affinity purified rabbit anti-mouse IgG (Cappel Laboratories) (1.6 µg/ml, incubated 1 hr. washed 3×, then $^{125}$I-protein A (Pharmacia, labeled by chloramine T method to 40–50 µCi/µg) 40,000 cpm/well was added, incubated 1 hr., washed 8× in PBS, and autoradiographed overnight at −80° C. on XAR5 film with lighting plus intensifying screen (DuPont).

B. CHARACTERIZATION OF HYBRIDOMAS HAVING ANTI-BN ACTIVITY—EXTENSIVE EVALUATION ON SOLID-PHASE BOMBESIN-LIKE PEPTIDES VERSUS INDIFFERENT PEPTIDES (SEE TABLE 1 AND FIG. 2)

Peptides (all purchased from Peninsula Laboratories) were adsorbed to 96 well polyvinyl chloride microtiter plates (Dynatech) by adding 0.05 ml of a 10 µg/ml peptide in phosphate buffered saline (PBS) for 1 hr., washing in PBS, then blocking with a 1% bovine serum albumin (BSA) PBS solution. Purified 2A11 from ascites fluid (10 µg/ml) was added, incubated, washed three times, then protein A affinity purified rabbit anti-mouse IgG (Cappel Laboratories) 1.6 µg/ml) was added, incubated, washed three times, then $^{125}$I-protein A (Pharmacia, labeled by chloramine T method to 40–50 µCi/µg) 40,000 cpm/well was added, incubated, washed 8× and then the wells cut out and counted in a Beckman gamma counter. All incubations were for 1 hr. at room temperature in PBS with 1% BSA in 0.025 ml volumes.

Percent cross reactivity was determined as follows:

% cross reactivity—cpm$^{125}$I-protein A bound on peptide target minus cpm bound on BSA target divided by crop bound by bombesin minus BSA background times 100. Typically, the bombesin target caused 2A11 binding sufficient to bind about 32,776 cpm of $^{125}$I-protein A while the BSA background bound about 30 cpm.

C. QUANTITATIVE INHIBITION ASSAY FOR THE DETECTION OF BOMBESIN-LIKE PEPTIDES. (See FIG. 3)

Antibodies 2A11 or MOPC 21 were adsorbed to 96 well polyvinylchloride plates at 500 ng/well followed by saturation with 1% BSA-PBS. Unlabeled bombesin was added to triplicate wells covering a range from 1–1,000 pg and incubated for 1 hr. at room temperature. Without removing the unlabeled bombesin samples, about 12,000 cpm of $^{125}$I-Tyr$^4$-bombesin was added to each well and incubated overnight at 4° C., washed 8× and counted. All additions were in 1% BSA-PBS in a 25 µl volume, and the washes were with 1% BSA-PBS 0.2 ml/well. Substance P over a similar concentration range does not generate a significant deflection of the quantitative curve.

D. QUANTITATION OF BOMBESIN-LIKE PEPTIDES IN SCLC AND NON-SCLC CELL CULTURE LINES

For preparation of cell extracts for RIA, 1–5×10$^7$ cells were washed thrice in PBS, pelleted and resuspended in 1 ml of 2M acetic acid, homogenized in a Brinkman Polytron, heated in a boiling water bath for 15 mins., clarified by centrifugation at 3,000 rpm, and the supernatant lyophilized, and stored at −80° C. The freeze dried extract was resuspended in 0.5 to 1 ml PBS and reclarified, and protein concentration determined (Bio-Rad assay kit). Dilutions of this extract were tested by the quantitative inhibition radioimmunoassay described supra.

E. CLONOGENIC ASSAY TO EVALUATE THE EFFECT OF 2A11 ON SCLC GROWTH IN VITRO

Assays were performed in serum-free HITES (Gibco, N.Y.) medium according to the protocol of Carney, et al. *Proc. Natn, Acad. Sci. USA* 78, 3185–3189, (1981). A single cell suspension of target cells (NCI-N592 or NCI-417) taken from log-phase cultures were mixed with 0.3% agarose in HITES (v/v) in the absence or presence of antibody (MOPC 21 versus 2A11) and plated over a pre-hardened base layer of 0.5% agarose/HITES. Because of its poor colony forming efficiency in serum-free medium, NCI-N417 culture plates were supplemented with 0.1% BSA to enhance cell growth, NCI-N592 cells were seeded at $5 \times 10^4$ per plate while NCI-N417 cells were plated at $1 \times 10^4$. Plates were pre-screened to verify single cell distribution of test cells and assessed 21 days later for colony formation. Cell aggregates of greater than 50 cells were scored positive as definitive colony growth.

F. RECEPTOR BINDING ASSAY

-$^{125}$I-Tyr$^4$-bombesin (about 40,000 cpm per test) was incubated with the indicated concentrations of 2A11 for 60 mins. at 25° C. Then receptor binding assays were conducted using 10 mg wet weight of crude rat brain homogenate or $2 \times 10^6$ cells of SCLC line NCI-H345 and processed as described by Moody, at al. *Proc. Natn. Acad. Sci. USA* 75, 5372–5376 (1978) and Moody, et al. *Peptides* 4, 683–686 (1983). The difference in binding in the absence and presence of an excess unlabeled bombesin (1 μM) was taken as a measure of specific binding.

An important initial aspect in the preparation of anti-bombesin monoclonal antibody of the present invention resides in first preparing a conjugate of bombesin with bovine serum albumn (BSA). Various conjugation techniques are known in the art, but a part of the invention resides in obtaining a suitable conjugate which will produce the desired results. For instance, when gluteraldehyde was used as a cross linking agent, a suitable conjugation did not result. However, when carbodiimide was employed as a cross linking agent, a lys-3-BN conjugate with BSA was obtained which successfully induced immune reaction in the mice. In contrast, when the gluteraldehyde mediated conjugate was used to induce antibody in mice, anti-bombesin antibodies were not detected.

A successful method for obtaining a lys-3-BN-BSA conjugate, is now described. It should be noted that the free peptide (BN or lys-3-BN) is too small to produce antibody. Therefore, conjugation is required.

Five mg synthetic amphibian sequence lys-3-BN (Sigma Chemical, St. Louis, Mo.) is reacted with 10 mg BSA and 100 mg ethyl-3-(3-dimethyl amino propyl) carbodiimide hydrochloride for 15 minutes in an aqueous medium at ambient temperature, then dialyzed against distilled water to remove unconjugated peptide and excess carbodiimide. The lys-3-BN-BSA conjugate thus obtained was then utilized to challenge BALB/C mice. An intraperitoneal injection dosage of 100 mg BN equivalent per challenge is used once monthly for 3 consecutive months. Three days after the last injection, mouse spleen cells are fused to a myeloma cell line X63-AG8.653 following routine hybridoma technique.

Figure 2:
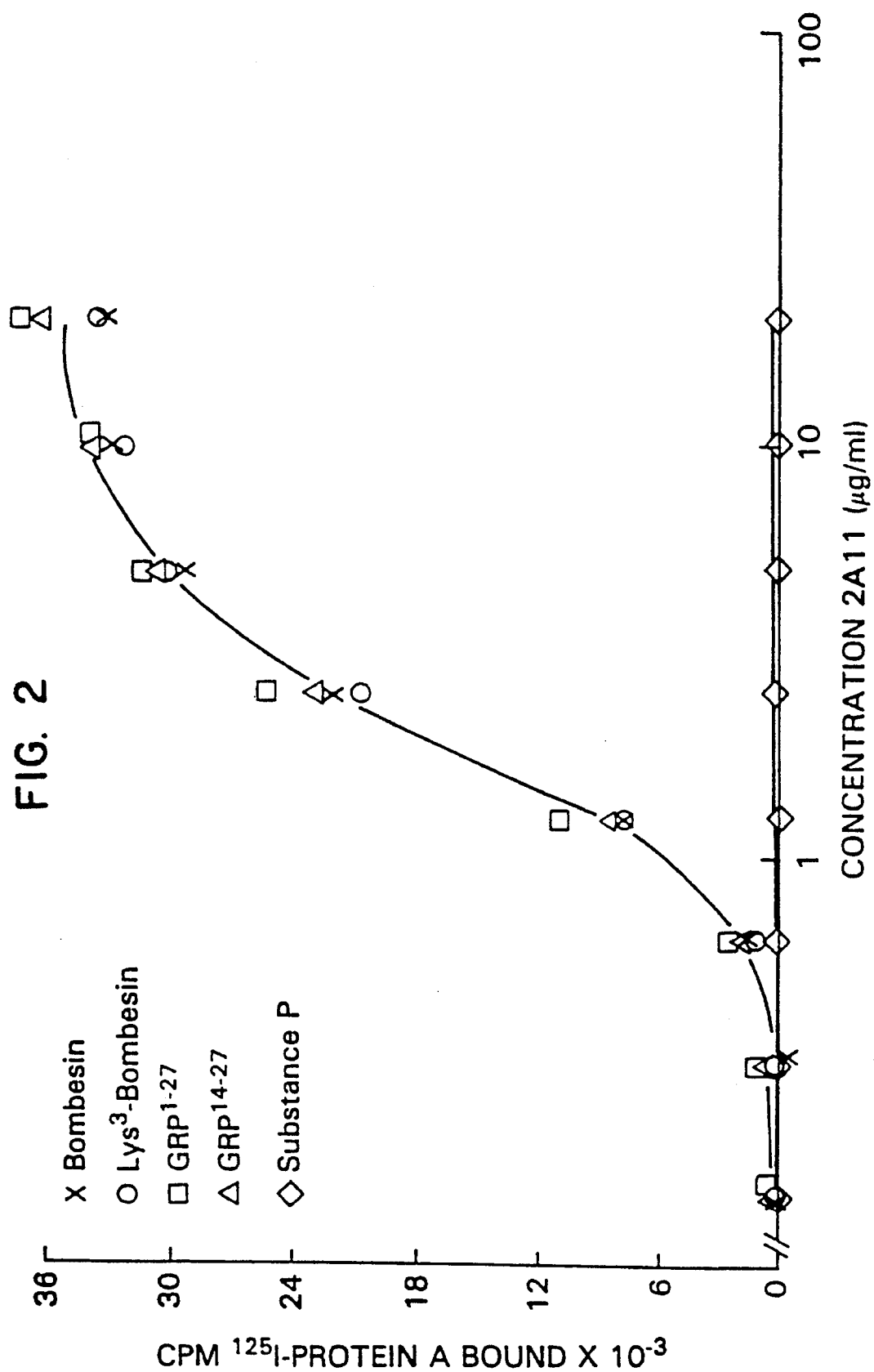
FIG. 2 shows titration binding curve of monoclonal antibody 2A11 to various solid phase synthetic peptides. The results represent the average of triplicate determinations with standard deviations being less than 5% for each point.

To be assured of the isolation of a desirable hybridoma, the following critical screening strategy and criteria were employed. The antibodies should react with BN or BN-like peptides (e.g. gastrin releasing peptide, GRP) but not cross-react with a similar peptide hormone, e.g. substance P, which has only two amino acids in common with BN, i.e. leucine and methionine as shown in FIG. 2. In other words, the monoclonal antibody should have such specificity as not to react with a peptide if there is alteration or lack of identity at the carboxy-terminal heptapeptide region of BN (FIG. 1).

The following strategy was, therefore, employed to isolate a hybridoma capable of producing monoclonal antibodies having the desired properties.

Hybrids were screened for anti-BN activity ten days following fusion by indirect radioimmunoassay on solid phase target plates coated with either bombesin, substance P or BSA. (Catt, K. et al. *Science* 158: 1570–1572, (1967). Substance P was chosen as an initial test peptide since it has the same carboxy-terminal dipeptide as bombesin. Hybridomas showing selective binding for bombesin were stabilized by "minicloning" (Nowinski, et al. *Virology* 93: 111–113, 1979.) and single cell cloned by limiting dilution (Minna, et al. *In Vitro* 17: 1058–1064, 1981). Of the original 908 hybrids produced and tested, only 6 clones remained stable and continued to produce anti-bombesin activity. One of these clones, designated as 2A11, expressed minimal cross reactivity with substance P and was, therefore, chosen for further characterization. Antibody 2A11 was identified as a mouse immunoglobulin subclass IgG1 kappa and was shown to react with many BLP found in amphibian, avian and mammalian species.

Initial characterization studies of 2A11 were carried out using ammonium sulfate-purified ascites preparation of the antibody. Assessed by indirect radioimmunoassay (RIA) Table 1 demonstrates differential binding property of antibody 2A11 for BLP verus unrelated peptides. Bombesin and its Lys$^3$ and Tyr$^4$ analogs elicit maximal binding of 2A11 as does the gastrin releasing peptide (GRP). Peptides expressing the same C-terminal dipeptide as bombesin, e.g. substance P, eledoisin, physalaemin and kassinin, showed less than 0.3% cross reactivity with antibody 2A11. Unrelated peptides also demonstrated minimal binding by 2A11 covering a range of cross reactivity from 0.001%–0.07%. FIG. 2 illustrates the t,180
titration curve of 2A11 binding to solid phase bombesin or GRP and their analogs as compared to substance P. Maximum binding to BLP was established at 10–20 μg/ml of the antibody with minimal binding still observed at 0.5 μg/ml. In contrast substance P showed insignificant 2A11 binding at all test concentrations of the antibody.

Having thus found a suitable hybridoma (HB 8711) capable of producing antibodies which specifically bind with BN or BLP without cross-activity with other similar peptides, further characterization and various applications therefore are now described.

Figure 3:
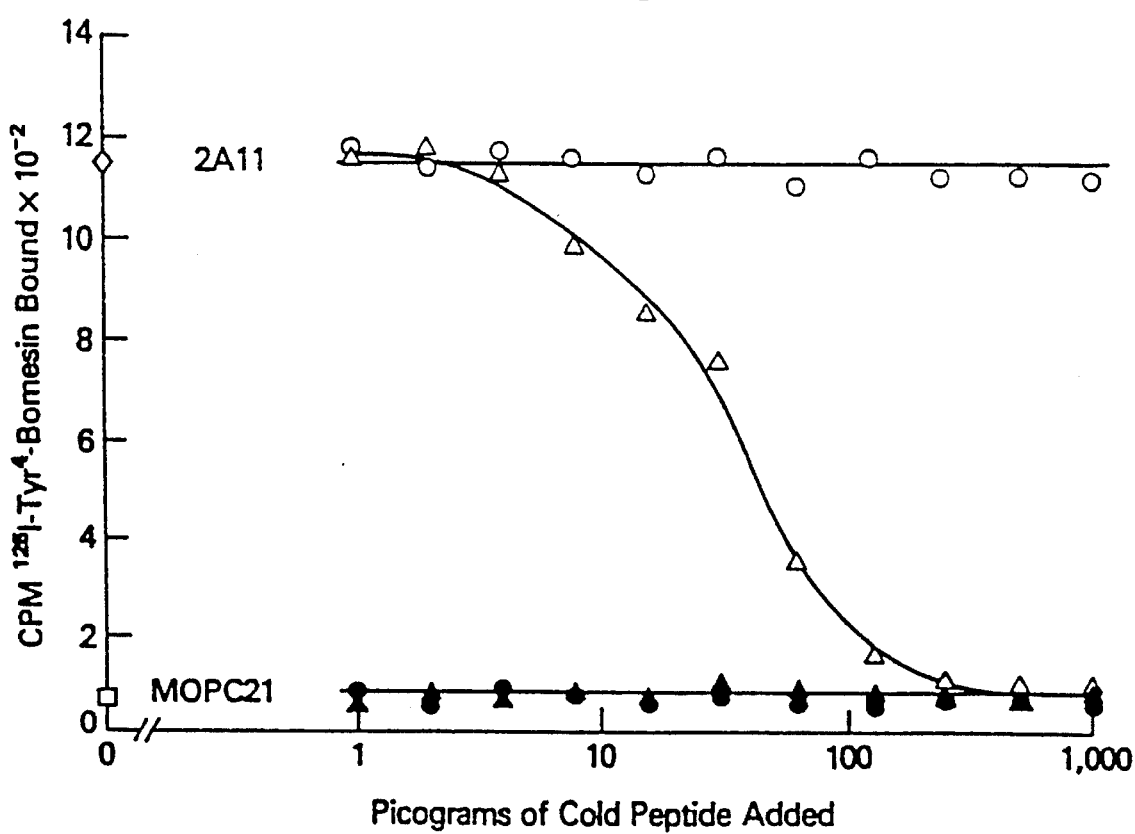
FIG. 3 shows quantitative inhibition assay to detect BLP. Substance P over a similar concentration range does not generate a significant deflection of the quantitative curve. Maximum binding of $^{125}$I-Tyr$^4$-bombesin labeled ligand to the respective solid phase antibodies (2A11 & MOPC 21) is indicated by open figures on the "Y" axis.
Figure 4:
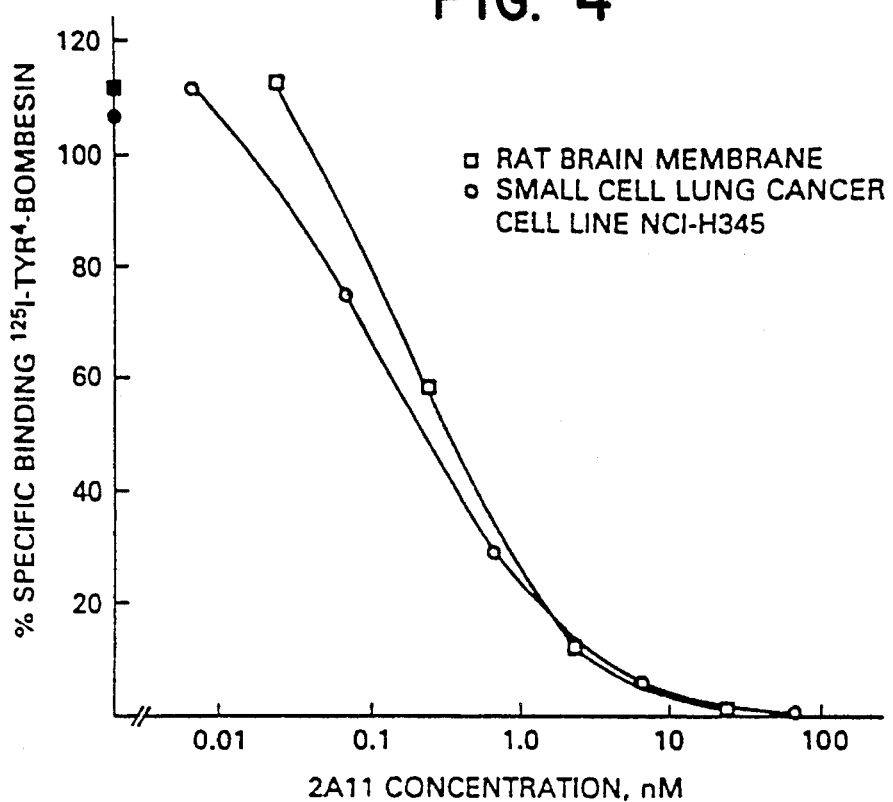
FIG. 4 shows inhibition of binding of labelled bombesin in a radioreceptor assay by monoclonal antibody 2A11. The shaded symbols on the "Y" axis show the effect of 67 nM MOPC 21 control antibody.

An approach employed in the characterization of this monoclonal antibody was to develop a quantitative assay system for BLP using solid phase 2A11 and $^{125}$-I-labeled Tyr$^4$-BN. (Catt, K. et al. *Science* 158: 1570–1572, 1967.) Demonstrated in FIG. 3 is the standard curve generated by displacement of iodinated ligand with increasing amounts of cold BN. The linear detection range of the assay covered a concentration of 5–100 pg of BN. Substance P over the same concentration range was incapable of inhibiting $^{125}$-Tyr$^4$-BN/2A11 binding and thus produced an insignificant deflection of the quantitative curve. Solid phase mouse myeloma protein MOPC 21 (IgG1 kappa) served as a specificity control for 2A11 and failed to bind the labeled peptide. t,200
This assay system was used to identify the antigenic determinant on BN responsible for 2A11 binding. This was accomplished by testing analogs of BN and ascertaining what modification in the synthetic peptides of BN leads to an inability to displace labeled ligand. These findings are summarized in Table 2 which verify the 2A11 recognition site to contain the C-terminal heptapeptide of BN. Alterations at the N-terminal region of BN (Lys$^3$, Tyr$^4$, Ala$^6$, Asn$^6$, NAGlY and GRP 20–27) did not significantly affect the analog's ability to inhibit $^{125}$I-Tyr$^4$-BN/2A11 interaction. In contrast modifications in the C-terminus of BN dramatically reduced the potency of the analog to displace the quantitative curve.

The regional localization of 2A11's recognition site for BN is most easily identified by examining the immune reaction elicited with the C6 fragment of BN (C-terminal hexapeptide) versus that observed for the C8 analog (GRP$^{20-27}$). The hexapeptide generates less than 1.0% inhibition of binding whereas the octapeptide approaches maximal inhibition (98.5% inhibited). When comparing the amino acid sequence of BN versus GRP (FIG. 1), it was noted that there existed an absolute homology at the C-terminal heptapeptide. It is this common sequence which is believed to be the minimal requirement for 2A11 binding and explains why BN, GRP$^{1-27}$, GRP$^{14-27}$, GRP$^{20-27}$, and alytesin produce t,220 maximal inhibition in the quantitative assay. Peptides which lack this heptapeptide sequence (unrelated structurally to BN) were shown to be impotent inhibitors of 2A11 binding (0.2% inhibition).

Utilizing quantitative assay as described supra, BLP products in the acid extracts of established human SCLC lines were determined (Table 3). A detectable range of 64±8 to 29,808±156 picograms (pg) of BLP per milligram of soluble protein was established for the ten SCLC lines tested (0.04–18.4 pM). These relative values are in agreement with previously reported quantitative data using rabbit anti-bombesin heterologous antiserum (Moody, et al. *Science* 214, 1246–1248 (1981). In contrast none of the non-SCLC lines (adenocarcinoma, large-cell carcinoma and squamous cell carcinoma) nor the non-lung cell lines (B-lymphoblastoid, T cell lymphoma and melanoma) expressed detectable levels of BLP (0.01 pM).

Antibody 2A11 was also used for immunohistochemical localization of BLP in paraffin embedded tissue. Using rabbit antisera it has been reported that chick proventriculus and human fetal bronchioles are rich in BN-like immunoreactivity. Use was, therefore, made of immunohistochemical staining technique of Hsu, et al. *J. Histochem. Cytochem.* 29, 557-5—1981, in combination with 2A11 for the light microscopic detection of BLP. Bombesinergic cells were found in chick proventriculus, human fetal bronchioles and a human SCLC. Immune staining was performed using 2A11 at 10 μg/ml. Specificity of 2A11 staining was verified by pre-absorption of the antibody solution with 100 μg/ml neurotensin (no inhibition of staining) or bombesin (staining inhibited).

Figure 5:
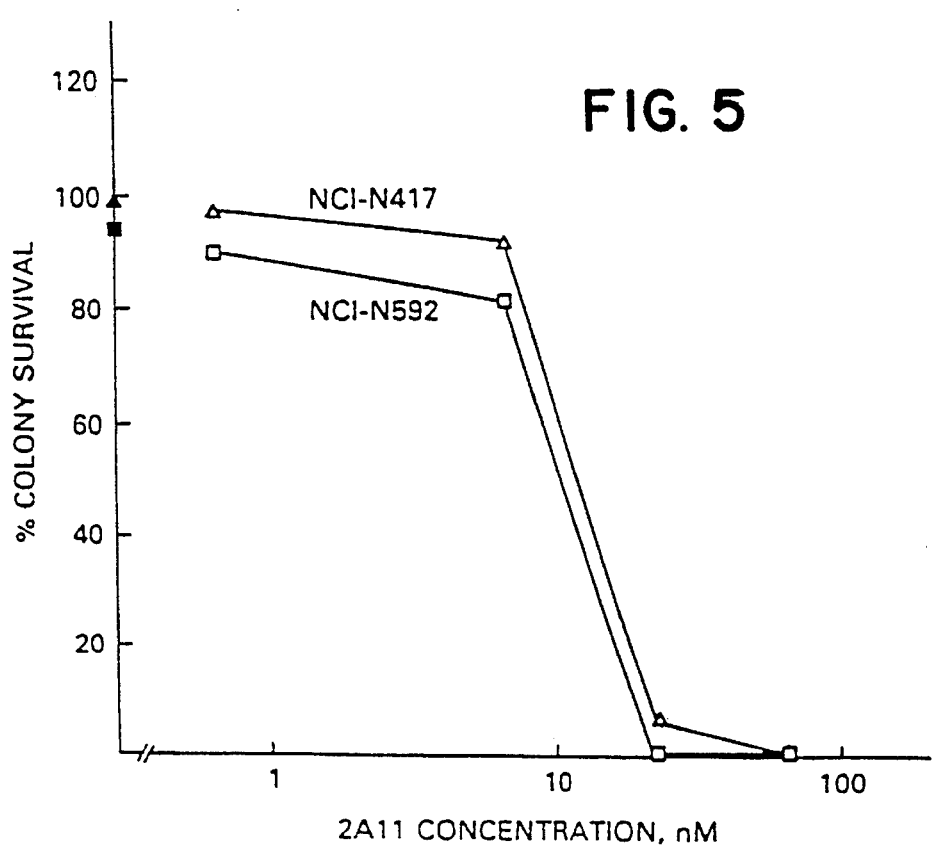
FIG. 5 shows inhibition of growth of human lung cancer cells in an agarose cloning assay by monoclonal antibody 2A11. All studies were done in triplicate and each point represents the mean colony count. For all studies the standard error was ±10%. Mouse myeloma protein MOPC 21 (indifferent antibody, IgG1 Kappa) at 67 nM failed to block SCLC growth as indicated by the shaped symbols on the "Y" axis.

The C-terminal deca-, nona-, and octa-peptides of BN have been implicated as the minimal size fragments required for full biological activity (River, et al. *Biochemistry* 17: 1766–1771, 1978; and Broccardo, et al. *Br. J. Pharmacology* 55: 221–117, 1975. In addition, BN's ability to interact with respective high affinity receptors on rat brain membranes (Moody, et al. *Proc. Natn. Acad. Sci. USA* 75, 5372–5376, 1978), pancreatic acinar cell (Jensen, et al. *Proc. Natn. Acad. Sci. USA* 75, 6139–6143, 1978) and human SCLC lines (Moody, et al. *Peptides* 4, 683–686, 1983) was shown to be dependent on the integrity of the C-terminal region. Since 2A11 binds to the same region of the peptide conveying biological potency, antibody's ability to interfere with BN/receptor interaction was determined. For this determination previously established receptor assays were used involving $^{125}$I-Tyr$^4$-BN and rat brain membranes or whole cell preparations of SCLC line NCI-H345 (Moody, et al. *Proc. Natn. Acad. Sci. USA* 75, 5372–5376, 1978; and Moody, et al. *Peptides* 4, 683–686, 1983). Antibody 2A11 was shown to block BN/receptor recognition in a dose related fashion (FIG. 5). In either assay system, 95 percent inhibition of BN binding occured with 10 nM of 2A11. An indifferent mouse myeloma protein (MPOC 21, same isotype as 2A11) at a 67 nM concentration did not significantly affect BN/receptor interaction (1% inhibition). Since maximal immune complexing by 2A11 can involve only two molecules of BN, the antibody induced blockage of receptor recognition could not be based on the artificial removal of labeled peptide (precipitation) but rather on the immune sequestration of the peptide's C-terminal end (steric hinderence). This indicated that 2A11 mimics the free receptor.

Monoclonal antibody 2A11 was then examined for its effect on the in vitro growth of SCLC cell lines using an agarose clonogenic assay containing serum-free HITES medium. Two cell lines derived from patients with documented SCLC disease (NCI-N417D and NCI-N592) were tested against varying nM concentrations of 2A11. The resulting dose response curves of these tests are presented in FIG. 5. The clonogenic growth of both cell lines was markedly inhibited by 2A11 at concentrations over 20 nM. Similar concentrations of MOPC 21 and heat denatured 2A11 showed insignificant inhibition of SCLC growth, <7% and <13% respectively (Table 4). In addition, when 50 nM of exogenous BN was introduced into the assay system, nullification of the 2A11 effect was observed. It is noted that the suppressive effect of 2A11 on SCLC growth is not due to direct cytotoxicity, since the antibody does not bind to intact (viable) SCLC cells (Table #1).

To demonstrate the potential therapeutic intervention of 2A11 on SCLC growth in vivo, nude mice heterotransplant studies were conducted. Two tumor cell lines were used in this study; a "classic" SCLC line, NCI-N592, which expressed typical small cell morphology and biochemical markers and whose growth in vitro was dependent on BLP; and a melanoma cell line, NCI-H234A, which was unresponsive to BN in vitro and served as a control. One week following their introduction into nude mice, each cell line produced a palpable tumor mass of 0.2–0.3 cm in diameter. The established tumors were then subjected to three experimental treatment trials (five mice each group) consisting of; 1) phosphate buffered saline (PBS), 2) MOPC 21; and 3) 2A11.

Figure 6A:
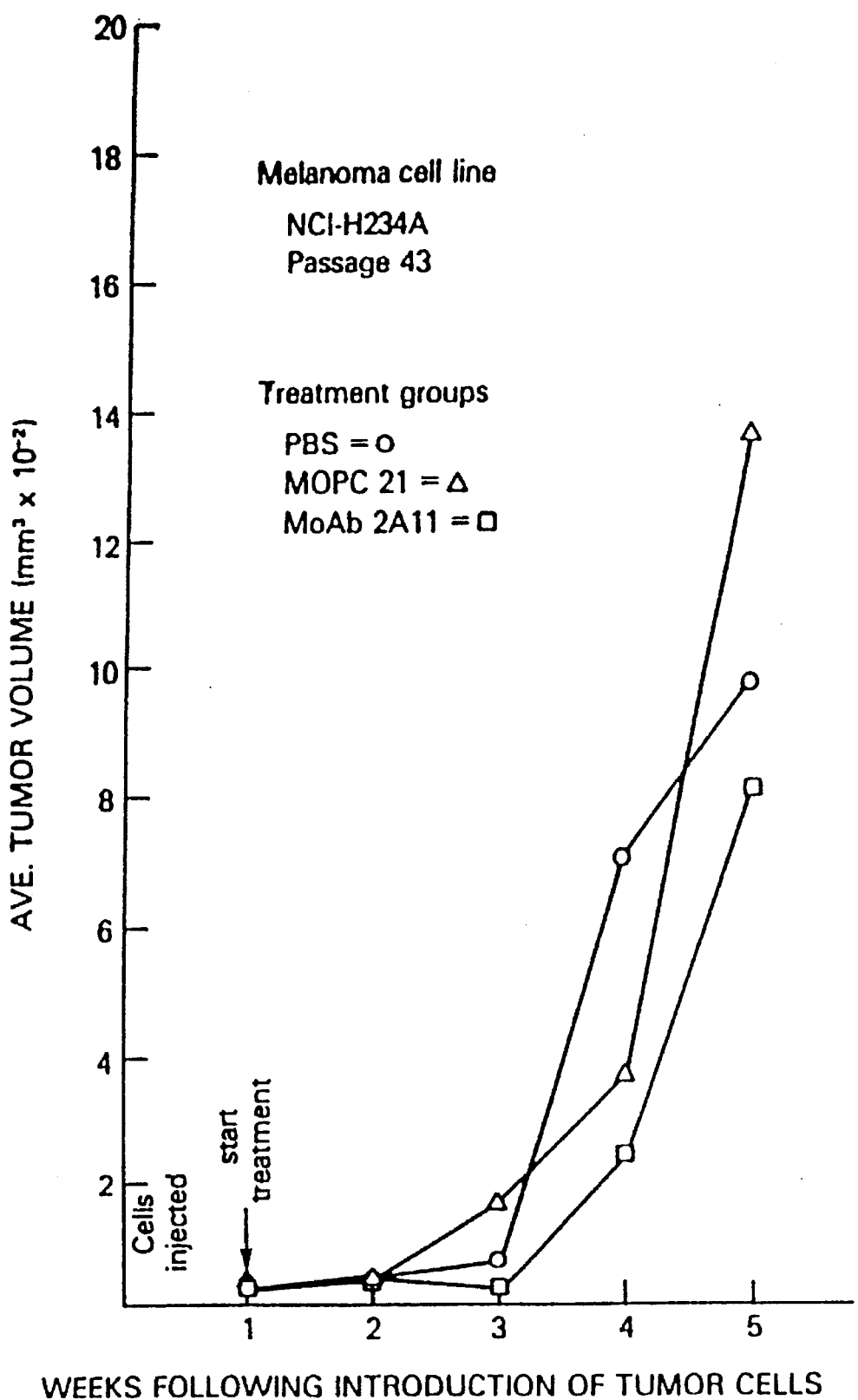
FIGS. 6a and 6b show effect of treatment with monoclonal antibody 2A11 on growth of human tumor xenografts in athymic nude mice.
Figure 6B:
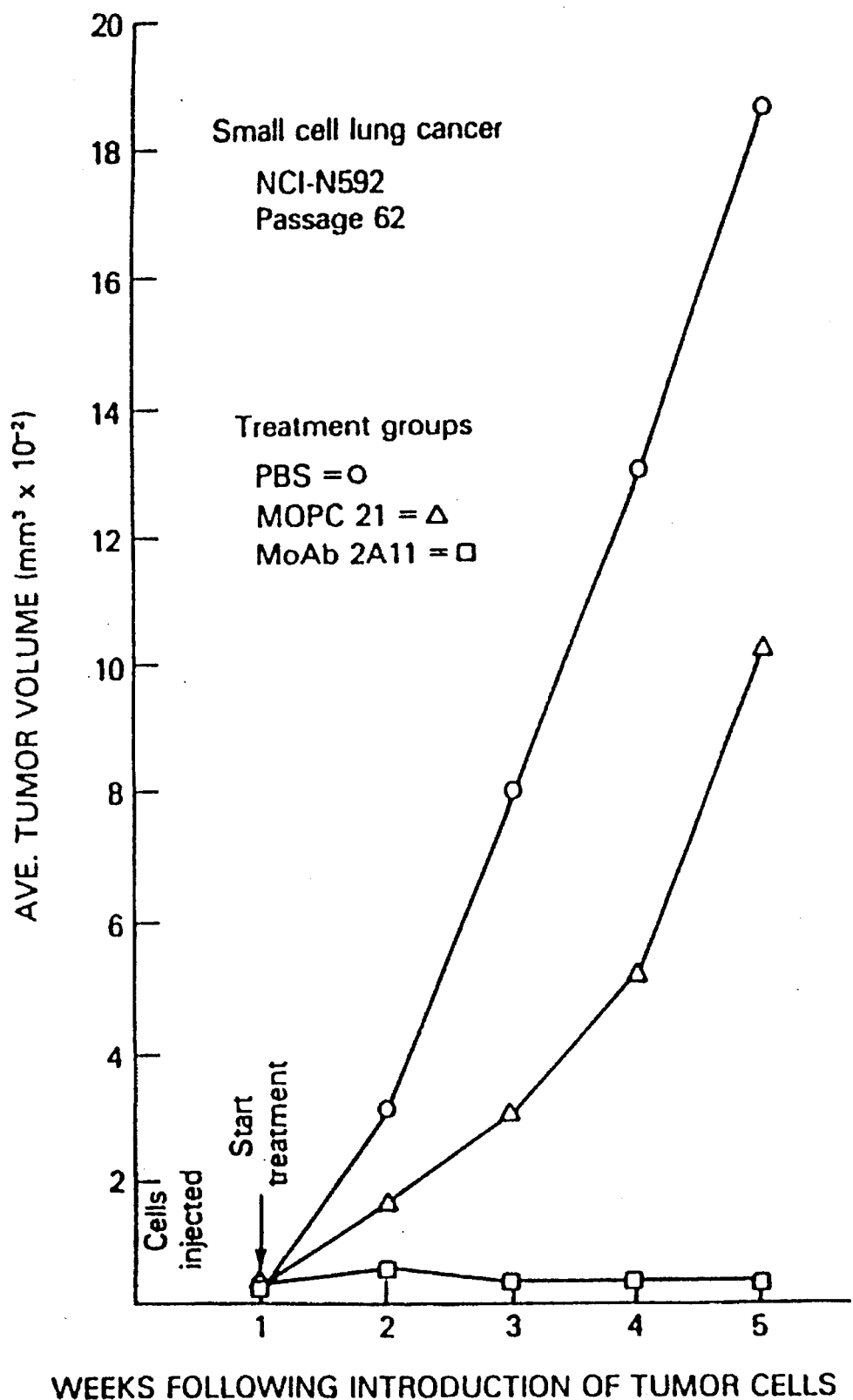

Treatment was administered via intraperitoneal t,270 injection 3 times weekly at 200 μg/0.5 ml/dose. Tumor growth was monitored as a function of volume over the next four weeks of continuous therapy (FIGS. 6a & 6b). The melanoma cell line, NCI-H234A, showed unhampered tumor growth in all three experimental groups with 5/5 mice from each group attaining an average tumor volume of 1000 mm by week 5. In contrast, dramatic suppression of SCLC growth (NCI-N592) was observed with 2A11 treatment (tumor mass in 5/5 mice [50 mm]) while control groups of MOPC 21 (4/5 mice) and PBS (5/5 mice) demonstrated rapid tumor growth in vitro and corroborated autocrine control of tumor proliferation.

The antibodies of the present invention also allows for the detection of anti-idiotypic antibodies in SCLC patient's serum by the BN-2A11 inhibition assay. By definition anti-idiotypic antibodies (anti-id) are anti-antibodies and express a second population of antibodies directed against primary antibody (Jerne, et al. *Ann. Immunol. (Inst. Pasteur)* 125C: 373–389, 1974). When this primary antibody is against a peptide hormone its appropriate anti-id can have anti-receptor activity. (Sege, et al. *Proc. Nat. Acad. Sci.* 75: 2443–2447, 1978). Since 2A11 mimics free BN receptor, by screening SCLC patient's sera in a BN-2A11 inhibition assay, one can detect 2A11 anti-ids with potential anti-receptor activity. Such screening strategy can be used for the early diagnosis of SCLC in patients.

In order to detect the presence of Anti-ID in the serum in a patient the following steps are followed:

(a) Patient serum is boiled for sufficient time in 2M acetic acid so as to precipitate the proteins and other precipitable components from the serum. The supernantant is then tested for the presence of bombesin using Quantitative inhibition assay (see FIG. 3).

When sera from normal subjects, from four SCLC patients and from subjects having other malignancies were tested for BN after acetic acid treatment as described above, all of them were found negative for BN. Results of such tests are shown in FIGS. 7(a,b).

(b) When a sample of the same sera as used in Step (a) above without acetic acid treatment were tested with solid phase bombesin assay, no anti-bombesin, antibody were detectable.

(c) However, when the same sere as employed in Step (b) above, i.e., without acetic acid treatment, were tested with solid phase 2A11 assay, three out the four SCLC sera positively reacted with solid phase 2A11, all other sera being negative.

The results obtained from this three-step test, indicate that the SCLC serum possesses such entity which binds with 2A11. This entity could not be BN or BLP because when tested for BN or BLP (Step (a) above), the results were negative.

Now, when protein A, which binds with antibodies of IgG series, is assayed using solid phase 2A11, no reaction took place. However, out of all the sere tested (normal, SCLC and other malignancies), only SCLC sere bound to 2A11 and in turn allowed for the binding of labeled protein A. This occurred in three out of the four human SCLC sera tested. These results clearly demonstrated the presence of anti-idiotypic antibody to 2A11 in the body fluid tested.

It is understood that the examples and embodiments described herein are for illustrative purposes only and that various modifications or changes in light thereof will be suggested to persons skilled in the art and are to be included within the spirit and purview of this application and scope of the appended claims.

A kit for screening the presence of SCLC in humans is one such example. Such a kit comprises containers containing monoclonal antibody of claim 1, anti-id antibody, microtiter plates, micropipettes, plate reader, instructions and other common accessories usually found in similar kits.

We claim:

1. A method of inhibiting growth of small cell lung cancer cells in a mammal, comprising the step of contacting said cells with a growth-inhibitory amount of a monoclonal antibody, wherein said antibody:

(i) binds bombesin or bombesin-like peptide specifically and is not cross-reactive with substance P;

(ii) has specificity for a peptide having the amino acid sequence of carboxyl terminal heptapeptide region Trp-Ala-Val-Gly-His-Leu-Met of bombesin; and (iii) blocks the binding of said bombesin or bombesin-like peptide to receptor therefor present on small cell lung cancer cells, said contacting performed under conditions such that said antibody binds said bombesin-like peptide and blocks binding of said peptide to receptor present on said cells.

2. A method according to claim 1, wherein said mammal is a human and said bombesin-like peptide is gastrin releasing peptide.

3. A method according to claim 1, wherein said antibody is a monoclonal antibody produced by hybridoma ATCC HB 8711.

\* \* \* \* \*